United States Patent [19]

Short

[11] Patent Number: 4,470,977
[45] Date of Patent: Sep. 11, 1984

[54] ANTIEMETIC AND ANTIPSYCHOTIC AGENTS

[75] Inventor: James H. Short, Dublin, Ohio

[73] Assignee: Adria Laboratories, Inc., Columbus, Ohio

[21] Appl. No.: 413,651

[22] Filed: Sep. 1, 1982

Related U.S. Application Data

[63] Continuation-in-part of Ser. No. 270,430, Jun. 4, 1981, abandoned.

[51] Int. Cl.³ .................... C07D 207/09; A61K 31/40
[52] U.S. Cl. .................................... 424/274; 548/567
[58] Field of Search ......................... 548/567; 424/274

[56] References Cited

U.S. PATENT DOCUMENTS

| 3,342,826 | 9/1967 | Miller et al. | 548/567 |
| 3,723,416 | 3/1973 | Thominet | 548/567 |
| 3,923,829 | 12/1975 | Denzler | 548/567 |
| 4,232,037 | 11/1980 | Florvall et al. | 548/567 |

OTHER PUBLICATIONS

Chem. Abs. 91:56811m; Ogata et al.; (1979).

*Primary Examiner*—Mark L. Berch
*Attorney, Agent, or Firm*—Biebel, French & Nauman

[57] ABSTRACT

Benzamide derivatives useful as antiemetic or antipsychotic agents are discussed. In the preferred embodiments, administration of the compounds is not accompanied by mammary hypertrophy.

4 Claims, No Drawings

ANTIEMETIC AND ANTIPSYCHOTIC AGENTS

CROSS REFERENCE TO RELATED APPLICATIONS

This application is a continuation-in-part of U.S. application Ser. No. 270,430 filed June 4, 1981, now abandoned.

BACKGROUND OF THE INVENTION

The present invention relates to benzamide derivatives which are useful as antiemetic and/or antipsychotic agents. In the preferred embodiments of the invention, administration of the agents is not accompanied by mammary hypertrophy.

U.S. Pat. No. 3,342,826 discloses numerous benzamide derivatives which are useful as antipsychotic and antiemetic agents. Among the compounds disclosed in the patent are 2-methoxy-N-(1-ethyl-2-pyrrolidinylmethyl)-5-sulfamoyl benzamide (so-called Sulpiride), 3,5 dichloro-N-(1-ethyl-2-pyrrolidinylmethyl)-2-methoxybenzamide, and 5-bromo-N-(1-ethyl-2-pyrrolidinylmethyl)-2-methoxy benzamide.

Benzamide derivatives function by blocking dopamine receptors. An undesirable side effect which accompanies the administration of prior derivatives like Sulpiride is mammary hypertrophy which is caused by an increase in the release of prolactin. Prolactin is formed and secreted by the pituitary gland and its release is regulated by prolactin inhibiting factor or PIF. PIF is found in the hypothalamus and there are indications that PIF is under dopaminergic control. Thus, it is believed that when the dopamine receptors are blocked by benzamide derivatives, PIF is not secreted and there is an elevation in prolactin levels which results in mammary hypertrophy.

The hormonal imbalance observed with sulpiride and its analogues raises questions as to the safety of the compounds. Many tumors and cancers are hormonally activated. Thus, it is possible that the administration of Sulpiride may trigger a neoplasm or worsen a pre-existing tumor. Moreover, breast engorgement, galactorrhea, and amenorrhea, which are caused by prolactin, are particularly troublesome side effects in female patients. Thus, there is a need for antiemetic and antipsychotic agents which do not cause mammary hypertrophy.

SUMMARY OF THE INVENTION

The present invention provides a number of compounds which are useful as antiemetic and/or antipsychotic agents, many of which can be administered effectively without mammary hypertrophy.

The invention compounds include:
1. 3-chloro-N-(1-ethyl-2-pyrrolidinylmethyl)-2-methoxybenzamide
2. 4-chloro-N-(1-ethyl-2-pyrrolidinylmethyl)-2-methoxybenzamide
3. 5-chloro-N-(1-ethyl-2-pyrrolidinylmethyl)-2-methoxybenzamide
4. N-(1-ethyl-2-pyrrolidinylmethy)-2-methoxybenzamide
5. N-(1-ethyl-2-pyrrolidinylmethyl)-2-methoxy-4-methylbenzamide
6. N-(1-ethyl-2-pyrrolidinylmethyl)-2-methoxy-5-methylbenzamide
7. N-(1-ethyl-2-pyrrolidinylmethyl)-2-methoxy-3-nitrobenzamide
8. N-(1-ethyl-2-pyrrolidinylmethyl)-3-methyl-2-nitrobenzamide
9. 2-amino-N-(1-ethyl-2-pyrrolidinylmethyl)-benzamide
10. 2-amino-N-(1-ethyl-2-pyrrolidinylmethyl)-3-methylbenzamide
11. 3-amino-N-(1-ethyl-2-pyrrolidinylmethyl)-2-methylbenzamide
12. 2,5-dichloro-N-(1-ethyl-2-pyrrolidinylmethyl)-benzamide
13. 3-chloro-N-(1-ethyl-2-pyrrolidinylmethyl)-2-methylbenzamide The foregoing compounds are not all equivalent in terms of their antiemetic and antipsychotic effects or in their lack of prolactogenic activity. Compounds 1, 2, 3, 4, 9 and 12 above have been shown to possess an antiemetic effect and to suppress apomorphine induced climbing behavior, an indicator of antipsychotic activity, without mammary hypertrophy.

In addition to the foregoing compounds, the present invention also includes their pharmaceutically acceptable salts and derivatives thereof in which the 1-ethyl group on the pyrrolidine ring is replaced by a methyl, propyl, or butyl group.

As a further embodiment of the present invention, pharmaceutical preparations containing the aforesaid compounds in therapeutically effective amounts are provided.

DETAILED DESCRIPTION OF THE INVENTION

The invention compounds are synthesized by condensing the appropriate benzoic acid derivative and amine in a conventional manner. The benzoic acid derivatives used in synthesizing the invention compounds include 3-chloro-2-methoxybenzoic acid, 3-methyl-2-nitrobenzoic acid, 4-chloro-2-methoxybenzoic acid, 2-amino-3-methylbenzoic acid, 3-amino-2-methylbenzoic acid, 3-chloro-2-methylbenzoic acid, 2-methoxybenzoic acid, 2,5-dichlorobenzoic acid, 5-chloro-2-methoxy-benzoic acid, 2-aminobenzoic acid, 2-methoxy-4-methylbenzoic acid, 2-methoxy-5-methylbenzoic acid and 2-methoxy-3-nitrobenzoic acid. Some of these acids are commercially available. Those that are not commercially available can be prepared from the commercial acids such as benzoic acid and 2-methoxybenzoic acid in a conventional manner.

Some typical examples of the synthesis of benzoic acid derivatives are provided in U.S. Pat. No. 3,342,826 and the acids used in making the invention compounds can be prepared in an analogous manner. 1-Ethyl-2-aminomethylpyrrolidine, which is typically used in forming the benzamide is a known compound.

The synthesis of 3-chloro-2-methoxybenzoic acid and 3-chloro-N-(1-ethyl-2-pyrrolidinylmethyl)-2-methoxybenzamide is illustrated in the following example:

SYNTHESIS EXAMPLE

A solution of 50 mL of concentrated $HNO_3$ and 150 mL of acetic anhydride was cooled to 5° C. 2-Methoxybenzoic acid, 15 g (0.1 mole), was added in small portions, and stirring was continued to 0.5 hour. A white solid precipitated and was collected. After two recrystallizations from ethyl acetate the product, 2-methoxy-3-nitrobenzoic acid, weighed 3.5 g (18%).

To a solution of 3.5 g (0.018 mole) of 2-methoxy-3-nitrobenzoic acid in 200 mL of dry methanol was added 15 drops of concentrated H₂SO₄. The solution was heated overnight and then evaporated. The solid residue was dissolved in ethyl acetate and washed twice with 5% NaHCO₃. The organic layer was dried, evaporated and the residue was crystallized from ethyl acetate-hexane to give 2.5 g (71%) of white solid, methyl 2-methoxy-3-nitrobenzoate, m.p. 50°–52°.

Reduction of 2.5 g (0.012 mole) of methyl 2-methoxy-3-nitrobenzoate in 150 mL of methanol was effected at low pressure over Raney nickel. Removal of the catalyst and solvent gave 2 g (91%) of the amino ester, methyl 3-amino-2-methoxybenzoate, as an oil which was not further purified.

A solution of 1.2 g of sodium nitrite in 3 mL of water was added dropwise to a solution of 2 g (0.011 mole) of methyl 3-amino-2-methoxybenzoate in 15 mL of conc. HCl kept below 10° C. After completing the addition, stirring was continued for 0.5 hour at 0° C. The cold solution was then added dropwise to a solution of 2.5 g of cuprous chloride in 6 mL of concentrated HCl at 80°–85° C. After stirring at this temperature for 0.5 hour, the solution was chilled to precipitate an oil which was taken up in methylene chloride. After drying and removing the solvent, the oil obtained above was dissolved in 75 mL of methanol containing 7 mL of 10% NaOH. The solution was heated under reflux for 0.5 hour. After evaporation, the oil was treated with 40 mL of dilute HCl. A white solid precipitated to give 0.5 g (24%) of 3-chloro-2-methoxybenzoic acid after crystallization from ethyl acetate-hexane.

A solution of 0.5 g (0.0027 mole) of 3-chloro-2-methoxybenzoic acid in 10 mL of thionyl chloride was heated under reflux for 2 hours and then evaporated to yield 3-chloro-2-methoxybenzoic acid chloride. The residual oil was dissolved in 20 mL of methlene chloride containing 0.4 g (0.003 mole) of 2-aminomethyl-1-ethyl-pyrrolidine and 1 mL of triethylamine. After 1 hour at room temperature, the solution was evaporated and treated with water. The oil which precipitated was taken up in methylene chloride, dried and evaporated. The residue was crystallized from ether-pentane to obtain 0.55 g (69%) of the invention compound, m.p. 55°–58°.

Anal. for $C_{15}H_{21}ClN_2O_2$: Calc.: C, 60.70; H, 7.13; N, 9.44. Found: C, 60.79; H, 7.21; N, 9.40.

The compounds of the present invention can be compounded with a suitable pharmaceutical carrier to prepare compositions suitable for administration. The compounds are preferable administered parenterally or orally in an amount of about 100 mg to 5 g per day and preferably 600 to 2500 mg per day. In most cases the compounds are used in the form of an acid addition salt such as the hydrochloride, phosphate, fumarate, citrate, tartrate or the like.

In the following examples, the antipsychotic activity of the invention compounds is demonstrated.

Sulpiride is used for comparison.

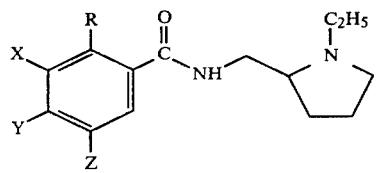

TABLE 1

| Compound | R | X | Y | Z |
|---|---|---|---|---|
| 1 | OCH₃ | Cl | H | H |
| 1 | OCH₃ | Cl | H | H |
| 2 | OCH₃ | H | Cl | H |
| 3 | OCH₃ | H | H | Cl |
| 4 | OCH₃ | H | H | H |
| 5 | OCH₃ | H | CH₃ | H |
| 6 | OCH₃ | H | H | CH₃ |
| 7 | OCH₃ | NO₂ | H | H |
| 8 | NO₂ | CH₃ | H | H |
| 9 | NH₂ | H | H | H |
| 10 | NH₂ | CH₃ | H | H |
| 11 | CH₃ | NH₂ | H | H |
| 12 | Cl | H | H | Cl |
| 13 | CH₃ | Cl | H | H |
| Sulpride | OCH₃ | H | H | SO₂NH₂ |

EXAMPLE 1

The effect of each of the compounds in Table 1 on apomorphine induced climbing behavior related to stimulation of dopaminergic receptors was studied under the experimental conditions described by Costetin et al, 1975, Rapid and Dissociated Changes in Sensitivities of Different Dopamine Receptors in Mouse Brain, *Nature*, 257, 405. Each mouse was injected with doses ranging from 6.25 to 100 mg/kg of the compound and antagonism was observed 20 minutes after an injection of 1 mg/kg s.c. apomorphine. The results are shown in Table 2. With the exception of compounds, 8, 10, 11 and 13, the invention compounds exhibit an antagonism to apomorphine induced climbing behavior, a possible measure of antipsychotic activity.

TABLE 2

| | Antagonism to Apomorphine Induced Climbing Behavior | |
|---|---|---|
| Compound | Antagonism (20 min. After) | ED₅₀ (mg/kg p.o.) |
| 1 | Yes | 26.8 (20.7–38.5) |
| 2 | Yes | — |
| 3 | Yes | — |
| 4 | Yes | — |
| 5 | Yes | — |
| 6 | Yes | — |
| 7 | Yes | — |
| 8 | No | — |
| 9 | Yes | — |
| 10 | No | — |
| 11 | No | — |
| 12 | Yes | — |
| 13 | No | — |
| Sulpiride | Yes | 24.3 (19.3–32.4) |

EXAMPLE 2

Female Sprague Dawley rats, obtained from Harlan Industries, and weighing 156–168 g, were randomly divided into groups of six rats each. The animals were individually caged during the 14-day study, with rat chow and tap water permitted ad libitum. The rat chow fed to the control group contained no drug, while that fed to the other groups contained 0.02% drug. Food cups were weighed and refilled on day 7 during the study. On day 14 of the study, the animals were sacrificed by asphyxiation in a CO₂ atmosphere and then were weighed. The abdominal skin was cut along the midline from the pelvis to the sternum and separated from underlying tissues by blunt dissection. Each animal was then examined grossly for mammary gland enlargement. The results in Table 3 below show that, at dosage levels approximately equal to those which consistently produce mammary hypertrophy in sulpiride-treated animals, the invention compounds fail to demonstrate such effects.

TABLE 3

Effect of Sulpiride and Sulpiride Analogs on
Mammary Gland Development in Female Sprague Dawley Rats

| Compound | n | Calculated Mean Dose ± SEM mg/kg/day | Number of Animals with Mammary Hypertrophy |
| --- | --- | --- | --- |
| 1 | 6 | 17.7 ± 0.40 | 0 |
| 2 | 6 | 16.6 ± 0.20 | 0 |
| 3 | 6 | 17.9 ± 0.6 | 0 |
| 4 | 6 | 18.3 ± 0.8 | 0 |
| 5 | 6 | 16.3 ± 0.73 | 0 |
| 6 | 6 | 18.4 ± 1.18 | 0 |
| 7 | 6 | 16.8 ± 0.51 | 0 |
| 8 | 6 | 15.4 ± 0.40 | 0 |
| 9 | 6 | 19.1 ± 0.7 | 0 |
| 10 | 6 | 16.2 ± 0.9 | 0 |
| 11 | 6 | 16.8 ± 0.25 | 0 |
| 12 | 6 | 19.6 ± 0.29 | 0 |
| 13 | 6 | 17.6 ± 0.20 | 0 |
| Sulpiride | 6 | 17.7 ± 0.33 | 6 |
| Control | 6 | | 0 |

EXAMPLE 3

Antiemetic Screen

Each compound is administered subcutaneously (sc) to two beagle dogs at 10.0 mg/kg. One hour following administration of the test compound, each animal receives 0.1 mg/kg, sc, of apomorphine HCl. Apomorphine consistently evokes an immediate emetic response through direct dopaminergic interaction at the medullary chemoreceptor trigger zone (CTZ). Antiemetic compounds which act at the CTZ and/or the midbrain vomiting center will block this effect of apomorphine. If both animals receiving a particular treatment are protected (i.e., no emetic response within one hour after apomorphine), the test compound is defined as active (+). In instances where protection is observed in only 1 of the 2 animals, the experiment is repeated in two additional animals and the results of the two tests are combined. Compounds which protect 3 out of 4 animals are then defined as active. The results are shown in Table 4 below and indicate that each of the invention compounds is active against emesis.

TABLE 4

Antagonism to Apomorphine Induced Emesis
In the Dog

| Compound | 10 mg/kg |
| --- | --- |
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |

Having described the invention in detail and with respect to specific embodiments thereof, it will be apparent that variations and modifications are possible without departing from the spirit and scope of the invention defined in the appended claims.

What is claimed is:

1. 3-chloro-N-(1-ethyl-2-pyrrolidinylmethyl)-2-methoxybenzamide and pharmaceutically acceptable salts thereof.

2. A pharmaceutical preparation useful as an antiemetic and/or antipsychotic agent comprising a therapeutically effective amount of 3-chloro-N-(1-ethyl-2-pyrrolidinylmethyl)-2-methoxybenzamide or a pharmaceutically acceptable salt thereof and a pharmaceutically acceptable carrier.

3. The pharmaceutical preparation of claim 2 wherein said composition contains said compound or salt in an antiemetically effective amount.

4. The pharmaceutical preparation of claim 3 wherein said composition contains said compound or salt in an antipsychotically effective amount.

* * * * *